United States Patent [19]
Isozaki et al.

[11] Patent Number: 5,364,561
[45] Date of Patent: Nov. 15, 1994

[54] LIQUID CRYSTAL COMPOUNDS AND LIQUID CRYSTAL COMPOSITIONS CONTAINING THEM

[75] Inventors: Tadaaki Isozaki; Hiroyuki Mogamiya; Yoshihiko Aihara; Takashi Hagiwara, all of Tokyo, Japan

[73] Assignee: Showa Shell Sekiyu Kabushiki Kaisha, Tokyo, Japan

[21] Appl. No.: 52,754

[22] Filed: Apr. 27, 1993

Related U.S. Application Data

[63] Continuation-in-part of Ser. No. 727,250, Jul. 11, 1991, abandoned.

[30] Foreign Application Priority Data

Jul. 13, 1990 [JP] Japan ................................ 2-185740

[51] Int. Cl.$^5$ ........................ C09K 19/12; C09K 19/52
[52] U.S. Cl. .......................... 252/299.65; 252/299.01
[58] Field of Search ....................... 252/299.01, 299.64, 252/299.65, 299.66, 299.67; 359/103, 104

[56] References Cited

U.S. PATENT DOCUMENTS

| | | | |
|---|---|---|---|
| 4,728,458 | 3/1988 | Higuchi et al. | 252/299.65 |
| 4,921,632 | 5/1990 | Nakamura et al. | 252/299.01 |
| 5,108,650 | 4/1992 | Koden et al. | 252/299.61 |
| 5,108,651 | 4/1992 | Terashima et al. | 252/299.61 |
| 5,110,496 | 5/1992 | Mogamiya et al. | 252/299.61 |
| 5,204,020 | 4/1993 | Suzuki et al. | 252/299.67 |
| 5,214,523 | 4/1992 | Nito et al. | 252/299.01 |

FOREIGN PATENT DOCUMENTS

| | | |
|---|---|---|
| 413989 | 2/1991 | European Pat. Off. |
| 0422613 | 4/1991 | European Pat. Off. |
| 3223390 | 10/1991 | Japan |

OTHER PUBLICATIONS

Patent Abstracts of Japan, vol. 11, No. 206 (C-433) [2653] (Jul. 3, 1987).

Y. Suzuki et al, Liquid Crystals, vol. 6: pp. 167–174 (1989).
Coates, The Influence of Alkyl Chain Branching on Smectic C Formation, Liquid Crystals, 2:63 (1987).
Suzuki et al, Fluorine–Containing Ferroelectric Liquid Crystal Compounds Showing Tristable Switching, Proc. 2nd International Conference on Ferroelectric Liquid Crystals, p. 106 (Jun. 27–30, 1989).
Suzuki et al, New Fluorine–Containing Ferroelectric Liquid Crystal Compounds With Large Spontaneous Polarization and Fast Switching Time, Proc. 12th International Liquid Crystal Conference, SY02 (Aug. 15, 1988).
Yamamoto et al, Switching Behavior in Antiferroelectric Liquid Crystals Under an Electric Field, Proc. 13th International Liquid Crystal Conference, FER-27-P-MON (Jul. 22–27, 1990).
Fujikawa et al, Antiferroelectric Liquid Crystal TFMHPOBC, Proc. 13th International Liquid Crystal Conference, FER-74-P-W/T (Jul. 22–27, 1990).

*Primary Examiner*—Shean Wu
*Attorney, Agent, or Firm*—Cushman, Darby & Cushman

[57] ABSTRACT

A liquid crystal compound represented by the following formula;

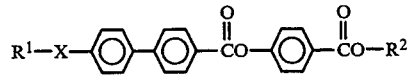

wherein $R^1$ and $R^2$ each represents an alkyl group having 3–20 carbon atoms, and X represents a group

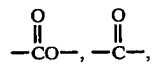

or —O—, or a single bond, and a liquid crystal composition exhibiting optically tristable states comprising the liquid crystal compound represented by the above formula and an antiferroelectric liquid crystal compound.

9 Claims, 3 Drawing Sheets

F I G. 1
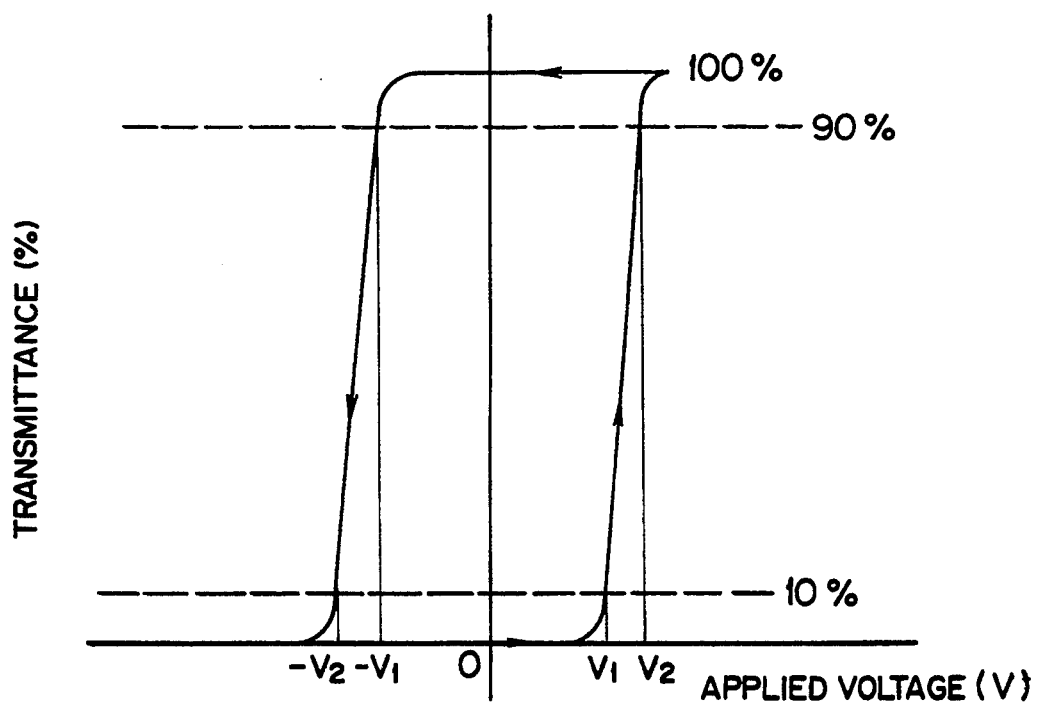
F I G. 2
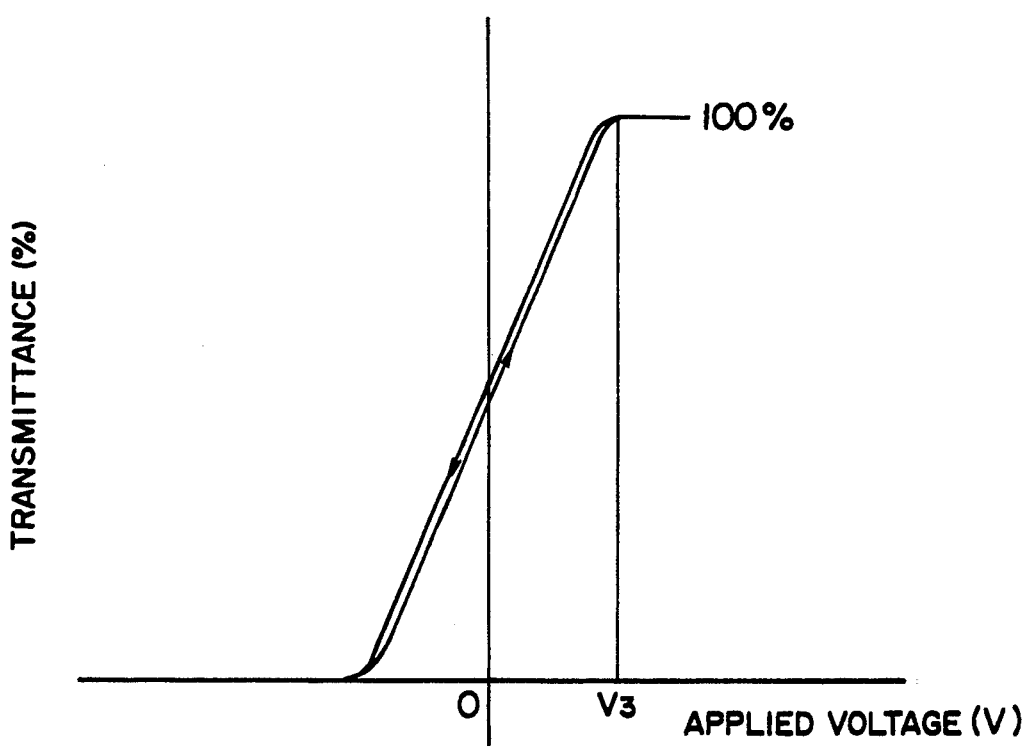

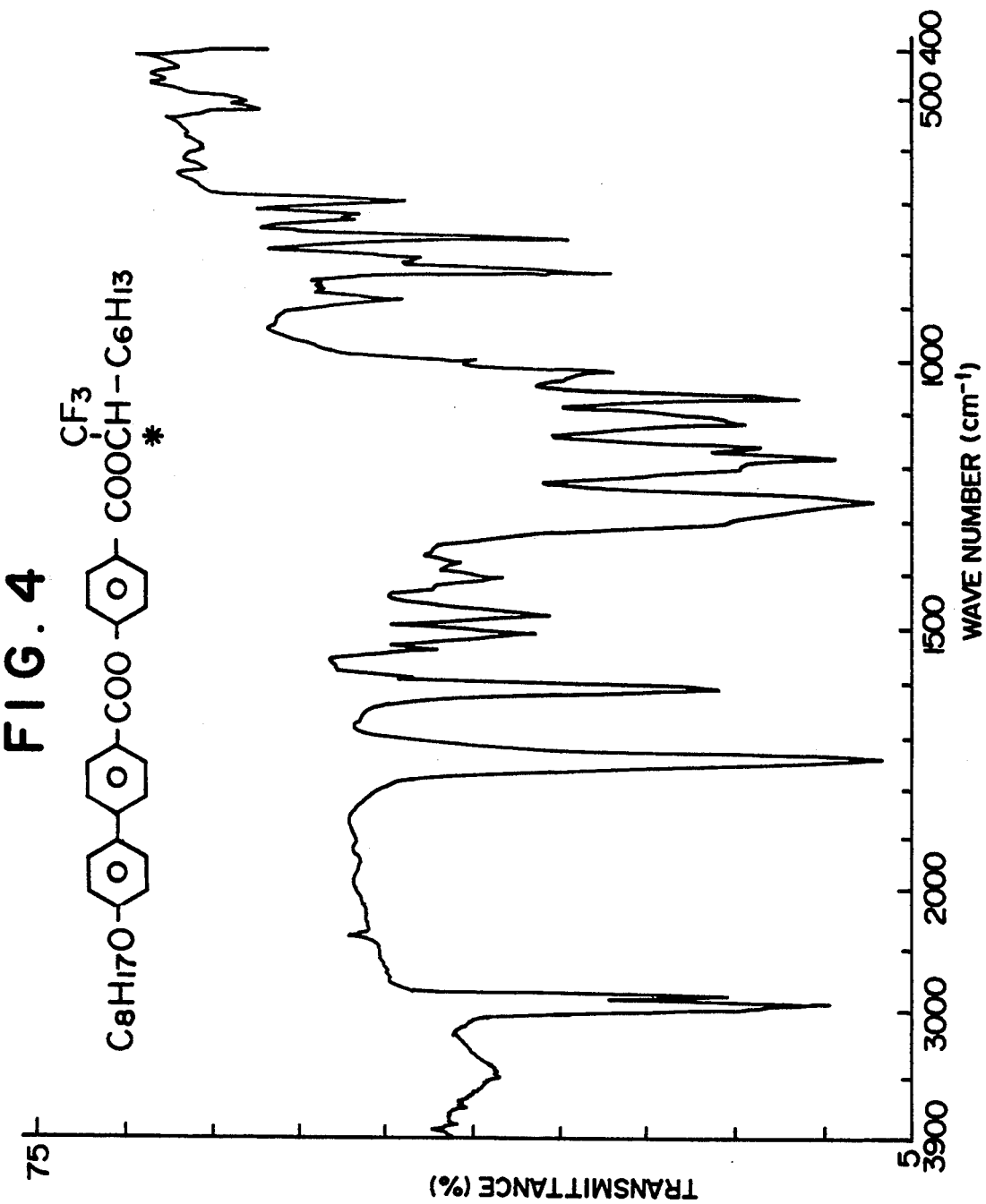

LIQUID CRYSTAL COMPOUNDS AND LIQUID CRYSTAL COMPOSITIONS CONTAINING THEM

Related Application

This is a continuation-in-part of U.S. patent application Ser. No. 07/727,250, filed Jul. 11, 1991 now abandoned.

Field of the Invention

The present invention comprises a liquid crystal composition containing an antiferroelectric liquid crystal compound, and the present liquid crystal composition is used for display devices or electro-optical devices which take advantage of the response to electric field.

Furthermore, the present invention relates to an antiferroelectric liquid crystal composition exhibiting tristable molecular alignments.

BACKGROUND OF THE INVENTION

As electrooptical devices comprising liquid crystals, electrooptical devices comprising nematic liquid crystals such as those of DSM, TN, G-H or STN types have been developed and put to practical use. These electrooptical devices comprising the nematic liquid crystals have a defect of a very slow response in the range from several milliseconds to several ten milliseconds and thus are limited in their applications. The slow response of devices utilizing a nematic liquid crystal is attributed to the fact that the torque for moving molecules is based on the anisotropy of dielectric constant and thus the power is not strong. Among these backgrounds, a ferroelectric liquid crystal which exhibits spontaneous polarization (Ps) and a strong torque based on Ps×E (E: applied electric field) and is capable of a high speed response in the range of several $\mu$ sec to several ten $\mu$ sec has been developed by Meyer et al. (Le Journal de Physique, 36, 1975, L-69). Furthermore, there is disclosed a ferroelectric liquid crystal in Japanese Patent Laid-Open Publication No. 307837/1988, there have already been proposed several high speed electrooptical devices comprising ferroelectric liquid crystals.

A typical example includes a device in which the helical structure is released by the force of wall faces and the two molecular alignments parallel to the wall faces is changed by the polarity of an applied electric field (see, for example, U.S. Pat. No. 4,367,924).

The aforementioned device is composed on the assumption of the presence of a compound which exhibits such an ideal bistable states as is shown by a field response wave pattern in FIG. 1. However, no compound which exhibits such an ideal bistable states as described above has been found, and bistable liquid crystal s synthesized hitherto show a field response wave pattern in FIG. 2 but not field response wave pattern in FIG. 1. It is the present state that if a device which exhibits a response wave pattern as shown in FIG. 2 is intended to be used for a switching circuit of light, such a pattern has a profile that transmittance varies gradually with the variation of an applied voltage from the minus side to the plus side and thus the object cannot be accomplished sufficiently with such a simple change of applied voltage as "on" and "off". Moreover, a bistable state liquid crystal having been synthesized is hard to form a monodomain structure as an ideal molecular alignment in the stage of an S*c phase at no electric field, and it causes disclination (defect) or twist which is the disturbance of the molecular alignment. It is thus difficult to realize the aforementioned ideal bistable alignment in a large area. Furthermore, it has a low threshold value (voltage at which the brightness varies at a predetermined extent), so that the dynamic drive of it may cause the lowering of contrast or the decrease of the range of viewing angle. The bistable state liquid crystal hitherto synthesized has no memory effect, since it cannot exhibit a hysteresis as shown in FIG. 1 but exhibits only a hysteresis as shown in FIG. 2. Thus, it is necessary to impress continuously a voltage at $v_3$ in FIG. 2 or to apply a high frequency in order to maintain a stable response in the S*c phase in the liquid crystal, and it cannot avoid a large energy loss.

Eventually, it is the present state that many problems remain unsolved in conventional ferroelectric liquid crystal electrooptical devices notwithstanding the earnest desire of a high speed liquid crystal electrooptical device which takes advantage effectively of an applied field and a bond having a strong molecular alignment obtained in a ferroelectric liquid crystal.

Thus, there have been conducted researches on liquid crystal compounds exhibiting tristable states, characterized in that the liquid crystal compound realizes a stable molecular alignment having a distinct light-dark contrast depending on electric field applied, generates a distinct threshold property and a distinct hysteresis as shown in FIG. 3, realizes easily dynamic drive and is capable of a high speed response.

As a result, there have been proposed livid crystal compounds having tristable states as disclosed in Japanese Patent Laid-Open Publications Nos. 316367/1989, U.S. Pat. No. 5 171 471 and U.S. Pat. No. 4 973 738.

However, the liquid crystal compounds represented by the formulae:

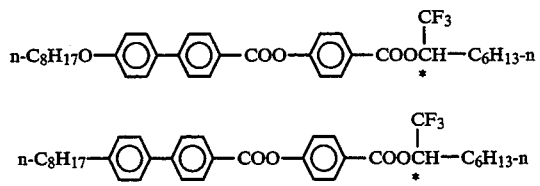

which are liquid crystal compounds exhibiting tristable states, have defects in their preparation processes that they are required for optical resolution and thus result in the expensive preparation costs because they are asymmetric compounds. As one of the methods for improving tile defects without diminishing the tristable states, there is a method for dilution and extending by adding other organic compounds. There is also another problem in this case that the tristable states are diminished by the addition of the other organic compounds in an amount of 20% or more, in some cases 10% or more.

SUMMARY AND OBJECTS OF THE INVENTION

The present invention comprises a liquid crystal composition which exhibits optically tristable states. This composition contains an effective amount of an antiferroelectric liquid crystal compound and a liquid crystal compound represented by the formula:

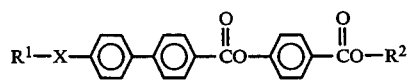

wherein $R^1$ and $R^2$ each represents an alkyl group having 3–20 carbon atoms, and X represents a

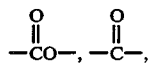

or —O—, or a single bond.

The object of the present invention is to provide a novel liquid crystal compound which is useful as a diluent of liquid crystal compounds exhibiting tristable states and exhibits per sea smectic phase.

Another object of the present invention is to provide a liquid crystal composition which employs a novel diluent and exhibits tristable states.

BRIEF DESCRIPTION OF THE DRAWINGS

FIG. 1 shows the hysteresis of an ideal bistable state liquid crystal which has not in fact been obtained, FIG. 2 shows the hysteresis of a practical bistable state liquid crystal having been hitherto synthesized, FIG. 4 shows the infrared spectrum (KBr) of the compound of Reference Example.

DETAILED DESCRIPTION OF THE INVENTION

Figure 3:
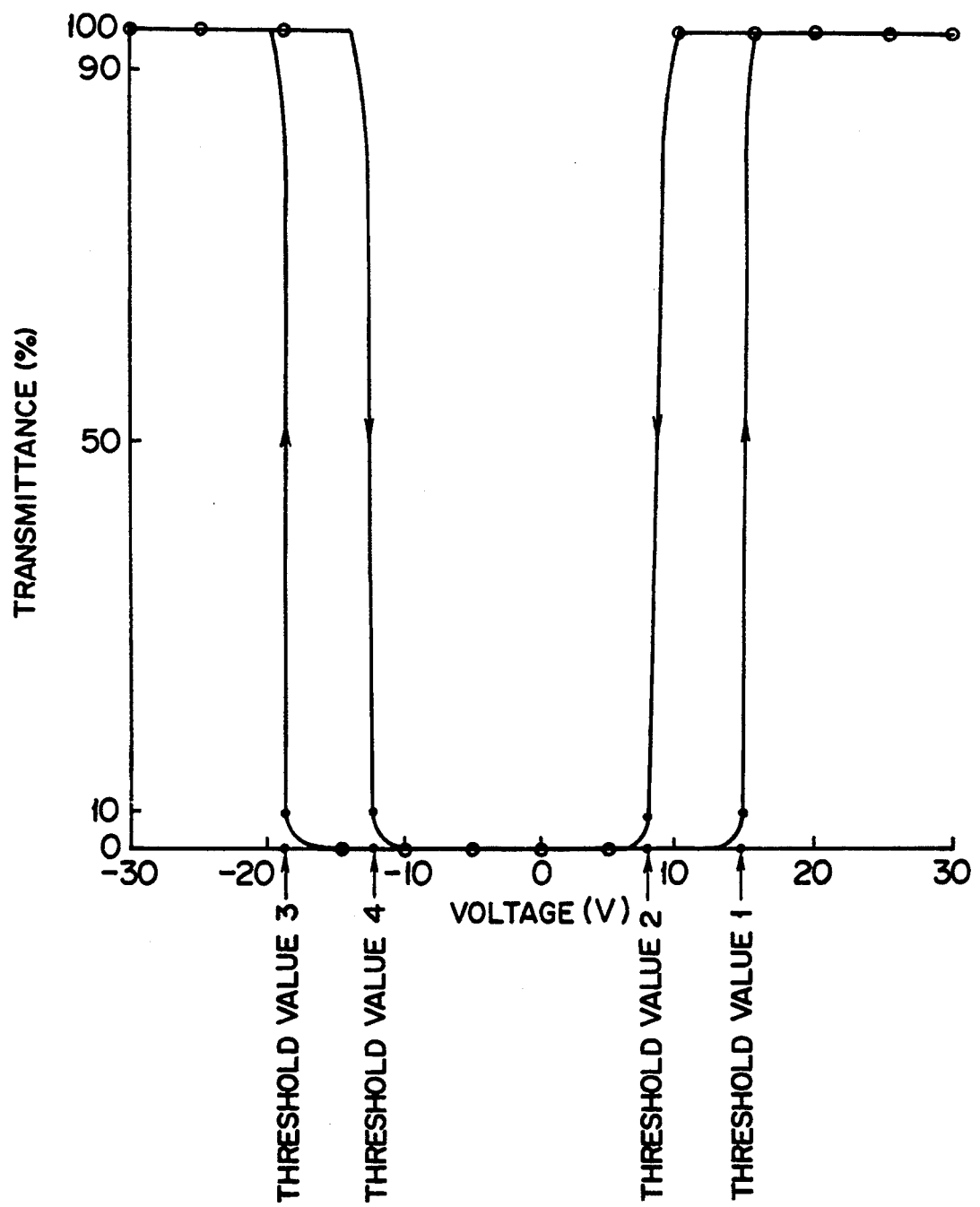
FIG. 3 shows the hysteresis of a tristable state liquid crystal composition according to the present invention, respectively, in which the abscissa represents applied voltage and the ordinate represents transmittance (%)

The present invention relates to a liquid crystal compound exhibiting a smectic phase represented by the formula

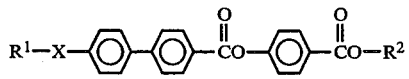 (I)

wherein $R^1$ represents an alkyl group having 3–20 carbon atoms, $R^2$ represents an alkyl group having 3–20 carbon atoms, preferably a normal alkyl group having 3–20 carbon atoms, and X represents a group

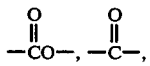

—O— or a single bond, and applications thereof.

The present invention also relates to a liquid crystal composition in which the liquid crystal compound represented by the formula [I] and an antiferroelectric liquid crystal compound are also incorporated.

The present invention further relates to a diluent represented by the formula [I] for liquid crystal compounds which exhibit S*(3) phase and tristable states.

The liquid crystal compound according to the present invention preferably includes the compounds represented by the formulae:

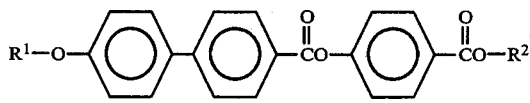

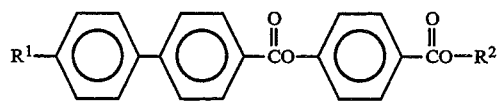

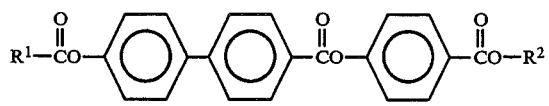

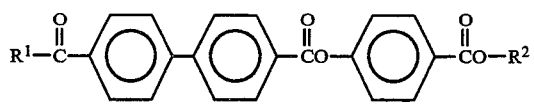

wherein $R^1$ and $R^2$ each represents an alkyl group having 3–20 carbon atoms and preferably $R^2$ represents a normal alkyl group having 3–20 carbon atoms.

Particularly, the liquid crystal compound according to the present invention is required to have such a skeleton structure as

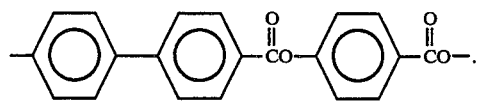

As the typical synthesis of the compounds according to the present invention, there are mentioned the methods as follows:

(1) 4-Hydroxybenzoic acid and an alkyl alcohol are subjected to an esterification reaction in the presence of sulfuric acid as a catalyst to give an alkyl 4-hydroxybenzoate. A 4'-alkyloxy-4-carboxybiphenyl is allowed to react with thionyl chloride to give a 4'-alkyloxybiphenyl-4-carboxylic acid chloride. The alkyl 4-hydroxybenzoate and the 4'-alkyloxybiphenyl-4-carboxylic acid chloride were allowed to react to give a 4-alkyloxycarbonylphenyl 4'-alkyloxybiphenyl-4-carboxylate; and (2) 4-Hydroxybenzoic acid and an alkyl alcohol are subjected to an esterification reaction in the presence of sulfuric acid as a catalyst to give an alkyl 4-hydroxybenzoate. A 4'-alkyl-4-carboxybiphenyl allowed to react with thionyl chloride to give a 4'-alkylbiphenyl-4-carboxylic acid chloride. The alkyl 4-hydroxybenzoate and the 4'-alkylbiphenyl-4-carboxylic acid chloride were allowed to react to give a 4-alkyloxycarbonylphenyl 4'-alkylbiphenyl-4-carboxylate.

In general, a variety of antiferroelectric liquid crystal compounds which exhibit tristable states can be usefully employed in the compositions of the present invention.

Preferable antiferroelectric liquid crystal compounds are represented by the following formulae;

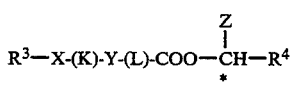

wherein $R^3$ and $R^4$ independently mean $C_3$ to $C_{20}$ alkyl groups; (K) and (L) are independently 1,4-phenylene group, 4,4'-biphenylene group, 2,6- or 2,7-naphthalene group,

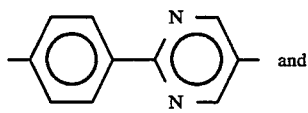 and
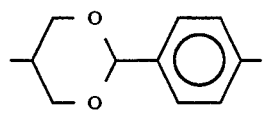
-continued
and the aryl group may be substituted by fluorine atom; X means —O—, —CO—, —COO—or direct bond; Y means —COO—or —CH$_2$—and Z means halogen substituted lower alkyl group. Examples of antiferroelectric liquid crystal compounds are shown below:
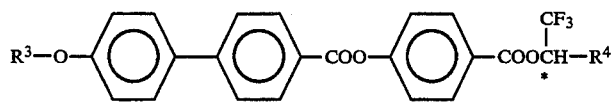
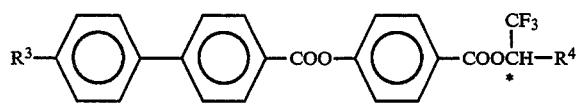
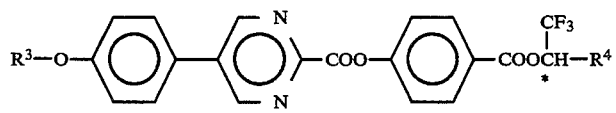
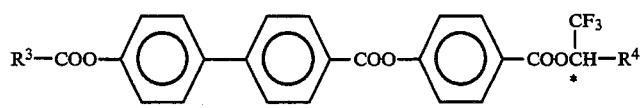
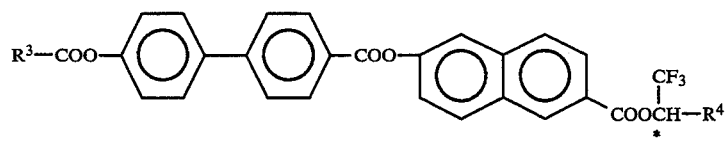
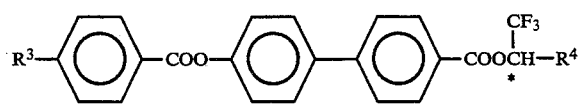
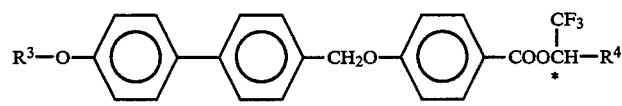
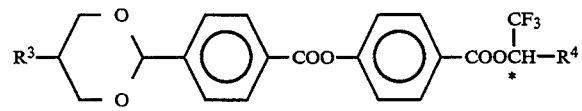
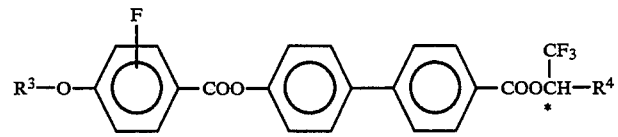
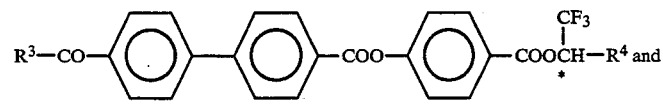

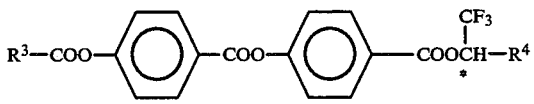

wherein R3 and R4 independently mean $C_3$ to $C_{20}$ alkyl groups. R3 is preferably $C_6$ to $C_{14}$ alkyl group and R4 is preferably $C_5$ to $C_{16}$ alkyl group. The trifluoromethyl group on the chiral carbon can, if desired, be replaced by $-C_2F_5$ or other comparably polar electron-withdrawing group, and spatially compatible group.

The antiferroelectric liquid crystal compound will generally comprise about 50% by weight or more of the present compositions.

The compounds and compositions of the present invention are described with reference to the following examples without limitation thereto.

EXAMPLE 1

1) Synthesis of n-nonyl 4-hydroxybenzoate

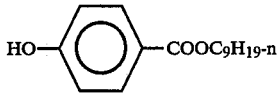

4-Hydroxybenzoyl chloride (5.52 g) was dissolved in 10 ml of dichloroethane, and a solution of nonyl alcohol (6.34 g) in 95 ml of dichloroethane was added. Several drops of concentrated sulfuric acid were added, and the mixture was heated under reflux for about 12 hours. The reaction mixture was poured into water, and the organic layer was separated, washed with water, a dilute aqueous $Na_2CO_3$ solution and water in this sequence and dried over anhydrous magnesium sulfate.

The solvent was removed by distillation to give 7.8 g of the desired product.

2) Synthesis of 4-n-nonyloxycarboxyphenyl 4'-n-decyloxybiphenyl-4-carboxylate

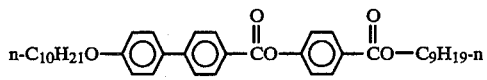

4'-n-Decyloxy-4-carboxybiphenyl (3.00 g) was heated under reflux for 6 hours together with an excessive amount of thionyl chloride, and the unaltered thionyl chloride was removed by distillation to give about 3 g of 4'-n-decyloxybiphenyl-4-carboxylic acid chloride.

The n-nonyl 4-hydroxybenzoate synthesized in the step 1) (1.40 g) and triethylamine (0.56 g) were dissolved in 30 ml of methylene chloride. The solution of the chloride synthesized above (2.18 g) in 35 ml of methylene chloride was added dropwise to the aforementioned solution at room temperature. Dimethylaminopyridine (0.19 g) was dissolved in 5 ml of methylene chloride and added further to the solution. The resulting mixture was heated under reflux for about 12 hours and then poured into water. Extraction was conducted with methylene chloride, and the organic layer was washed with water, an aqueous sodium carbonate solution and water in this sequence and dried over anhydrous magnesium sulfate. The solvent was removed by distillation, and the residue was purified by column chromatography (hexane: ethyl acetate=10:0.5) to give 1.07 g of the desired product.

The result of the NMR spectrographical analysis of the desired product are shown in Table 1.

TABLE 1

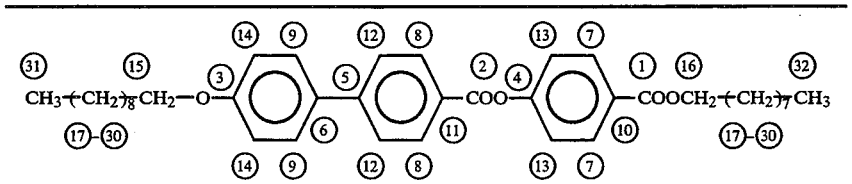

| Carbon | PPM | REMARKS |
| --- | --- | --- |
| 1 | 165.9 | carbon of ester carbonyl |
| 2 | 164.6 | carbon of ester carbonyl |
| 3 | 159.6 | aromatic ring carbon adjacent to oxygen |
| 4 | 154.6 | aromatic ring carbon adjacent to ester oxygen |
| 5 | 146.2 | aromatic ring carbon adjacent to aromatic ring |
| 6 | 131.8 | aromatic ring carbon adjacent to aromatic ring |
| 7 | 131.1 | aromatic ring carbon (for two atoms) |
| 8 | 130.8 | aromatic ring carbon (for two atoms) |
| 9 | 128.4 | aromatic ring carbon (for two atoms) |
| 10 | 128.1 | aromatic ring carbon adjacent to ester carbon |
| 11 | 127.0 | aromatic ring carbon adjacent to ester carbon |
| 12 | 126.6 | aromatic ring carbon (for two atoms) |
| 13 | 121.7 | aromatic ring carbon (for two atoms) |
| 14 | 115.0 | aromatic ring carbon (for two atoms) |
| 15 | 68.1 | methylene carbon adjacent to oxygen |
| 16 | 65.3 | methylene carbon adjacent to ester oxygen |
| 17 | 31.9 | methylene carbon |
| 18 | 31.8 | methylene carbon |
| 19 | 29.6 | methylene carbon |
| 20 | 29.5 | methylene carbon |
| 21 | 29.5 | methylene carbon |
| 22 | 29.4 | methylene carbon |

TABLE 1-continued

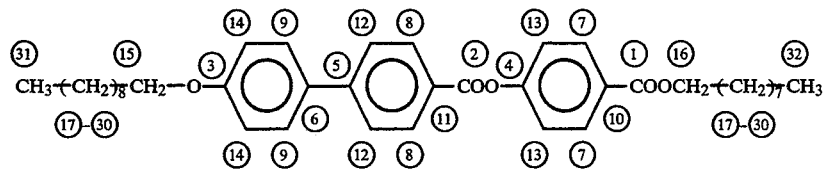

| Carbon | PPM | REMARKS |
|---|---|---|
| 23 | 29.3 | methylene carbon |
| 24 | 29.3 | methylene carbon |
| 25 | 29.2 | methylene carbon |
| 26 | 28.7 | methylene carbon |
| 27 | 26.0 | methylene carbon |
| 28 | 26.0 | methylene carbon |
| 29 | 22.7 | methylene carbon |
| 30 | 22.6 | methylene carbon |
| 31 | 14.1 | terminal methyl carbon |
| 32 | 14.1 | terminal methyl carbon |

3) The compound synthesized in Example 1 represented by the formula (A)

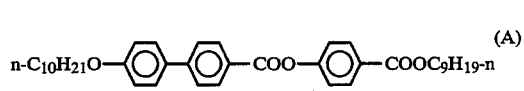

showed the following phase transition temperatures (° C.) on the observation with a polarizing microscope equipped with a hot stage:

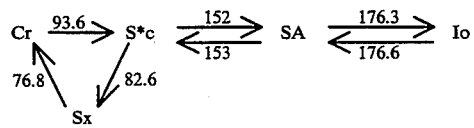

wherein
Iso: isotropic phase,
SA: smectic A phase,
S*c: smectic C phase,
Sx: smectic phase in a high order, and
Cr: crystal phase.

EXAMPLE 2

4-n-Nonyloxycarbonylphenyl 4'-n-decylbiphenyl-4-carboxylate

After 4'-n-decyl-4-carboxybiphenyl (3.10 g) was heated under reflux for 6 hours together with an excessive amount of thionyl chloride, unaltered thionyl chloride was removed by distillation to give about 3 g of 4'-n-decylbiphenyl-4-carboxylic acid chloride.

The n-nonyl 4-hydroxybenzoate (1.40 g) synthesized in the step 1) of Example. 1 and triethylamine (0.56 g) were dissolved in 30 ml of methylene chloride. The solution of the chloride synthesized above (2.10 g) in 35 ml of methylene chloride was added dropwise to the aforementioned solution at room temperature. Dimethylaminopyridine (0.19 g) was dissolved in 5 ml methylene chloride and added further to the solution. The resulting mixture was heated under reflux for about 12 hours and then poured into water. Extraction was conducted with methylene chloride, and the organic layer was washed with water, an aqueous sodium carbonate solution and water in this sequence and dried over anhydrous magnesium sulfate. The solvent was removed by distillation, and the residue was purified by column chromatography (hexane: ethyl acetate=10:0.5) to give 1.07 g of the desired compound.

The results of the NMR spectrographical analysis of the above compound are shown in Table 2.

TABLE 2

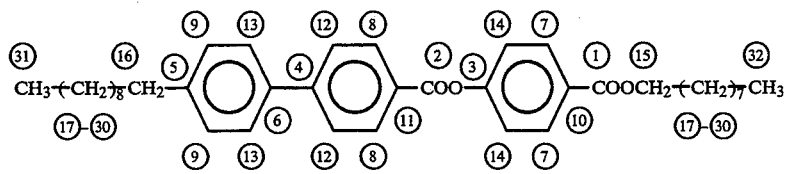

| Carbon | PPM | REMARKS |
|---|---|---|
| 1 | 165.9 | carbon of ester carbonyl |
| 2 | 164.5 | carbon of ester carbonyl |
| 3 | 154.6 | aromatic ring carbon adjacent to ester oxygen |
| 4 | 146.5 | aromatic ring carbon adjacent to aromatic ring |
| 5 | 143.5 | aromatic ring carbon adjacent to methylene carbon |
| 6 | 136.9 | aromatic ring carbon adjacent to aromatic ring |
| 7 | 131.1 | aromatic ring carbon (for two atoms) |
| 8 | 130.7 | aromatic ring carbon (for two atoms) |
| 9 | 129.0 | aromatic ring carbon (for two atoms) |
| 10 | 128.1 | aromatic ring carbon adjacent to ester carbon |
| 11 | 127.4 | aromatic ring carbon adjacent to ester carbon |

TABLE 2-continued

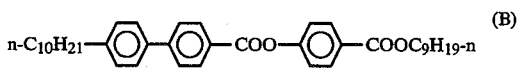

| Carbon | PPM | REMARKS |
| --- | --- | --- |
| 12 | 127.1 | aromatic ring carbon (for two atoms) |
| 13 | 127.0 | aromatic ring carbon (for two atoms) |
| 14 | 121.7 | aromatic ring carbon (for two atoms) |
| 15 | 65.2 | methylene carbon adjacent to ester oxygen |
| 16 | 35.6 | methylene carbon adjacent to aromatic ring |
| 17 | 31.9 | methylene carbon |
| 18 | 31.8 | methylene carbon |
| 19 | 31.4 | methylene carbon |
| 20 | 29.6 | methylene carbon |
| 21 | 29.6 | methylene carbon |
| 22 | 29.5 | methylene carbon |
| 23 | 29.5 | methylene carbon |
| 24 | 29.3 | methylene carbon |
| 25 | 29.3 | methylene carbon |
| 26 | 29.2 | methylene carbon |
| 27 | 28.7 | methylene carbon |
| 28 | 26.9 | methylene carbon |
| 29 | 22.7 | methylene carbon |
| 30 | 22.6 | methylene carbon |
| 31 | 14.1 | terminal methyl carbon |
| 32 | 14.1 | terminal methyl carbon |

4) The compound synthesized in Example 2 represented by the formula:

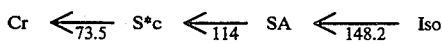 (B)

showed the following phase transition temperatures on the observation with a polarization microscope equipped with a hot stage:

Cr $\underset{73.5}{\rightleftarrows}$ S*c $\underset{114}{\rightleftarrows}$ SA $\underset{148.2}{\rightleftarrows}$ Iso wherein
Iso: isotropic phase,
SA: smectic A phase,
S*c: smectic C phase, and
Cr: crystal phase.

REFERENCE EXAMPLES

Synthesis of liquid crystal compounds exhibiting tristable states

REFERENCE EXAMPLE 1

Synthesis of 4-(1,1,1-trifluoro-2-octyloxycarbonyl)-phenyl 4'-n-octyloxybiphenyl-4-carboxylate

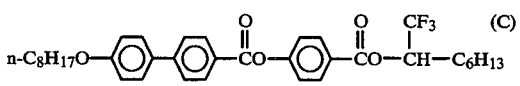 (C)

1) Synthesis of 1,1,1-trifluoro-2-octyl 4-benzyloxybenzoate

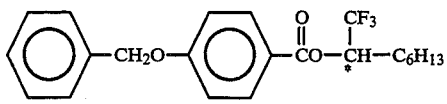

After 4-benzyloxybenzoic acid chloride (4.3 g) was dissolved in 50 ml of methylene chloride, a solution of an optically active 1,1,1-trifluoro-2-octanol (2.9 g), dimethylamino pyridine (0.6 g) and triethylamine (1.7 g) in 50 ml of methylene chloride was added portionwise under cooling.

The reaction mixture was allowed to raise the temperature to room temperature and subjected to reaction for a day. The reaction mixture was poured into ice-water, and extraction was conducted with methylene chloride. The methylene chloride layer was washed with a dilute hydrochloric acid, water, a 1N aqueous sodium carbonate solution and water in this sequence, and the organic layer was dried over anhydrous magnesium sulfate. The solvent was removed by distillation to give a crude product, which was purified by column chromatography on silica gel with toluene as an eluent and further recrystallized from ethanol to give 3.8 g of the desired compound.

2) Synthesis of 1,1,1-trifluoro-2-octyl 4-hydroxybenzoate

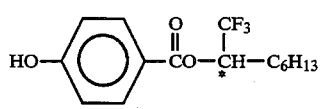

The compound obtained in the step 1) was dissolved in 100 ml of methanol, 0.4 g of a 10% Pd on carbon was added, and hydrogenolysis was conducted under the atmosphere of hydrogen to give 2.8 g of the desired compound.

3) Synthesis of 4-(1,1,1-trifluoro-2-octyloxycarbonyl)-phenyl 4'-n-octyloxybiphenyl-4-carboxylate

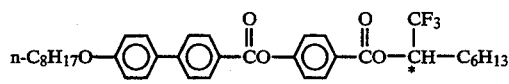

After 4-n-octyloxybiphenyl-4'-carboxylic acid (3.0 g) was heated under reflux together with an excessive amount of thionyl chloride for 6 hours, unaltered thionyl chloride was removed by distillation to give 4-n-octyloxybiphenyl-4'-carboxylic acid chloride.

To a solution of the acid chloride in 50 ml of methylene chloride was added slowly under ice cooling a solution of 1,1,1-trifluoro-2-octyl-4-hydroxybenzoate (2.8 g), triethylamine (1.0 g) and dimethylaminopyridine (0.3 g) in 50 ml of methylene chloride, and the mixture was allowed to react at room temperature for a day.

The reaction mixture was next poured into ice-water and extracted with methylene chloride. The methylene chloride layer was washed with a dilute hydrochloric acid, water, an aqueous sodium carbonate solution and water in this sequence and dried over anhydrous sodium sulfate. The solvent was removed by distillation to give a crude product, which was purified by column chromatography on silica gel with toluene as an eluent to give 2.1 g of the optically active desired compound.

For the measurement of the phase transition temperatures, the compound was further purified by recrystallization from anhydrous ethanol.

The infrared spectrum (KBr) of the desired product is shown in FIG. 4.

The compound synthesized in Reference Example represented by the formula;

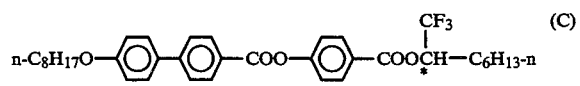

showed the following phase transition temperatures (° C.) on the observation with a polarizing microscope equipped with a hot stage:

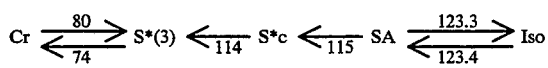

wherein
Iso: isotropic phase,
SA: smectic A phase,
S*c: chiral smectic phase,
S* (3): phase exhibiting tristable states, and
Cr: crystal phase.

REFERENCE EXAMPLE 2

See Example 5 of U.S. Pat. No. 5,110,496

Synthesis of the following compound

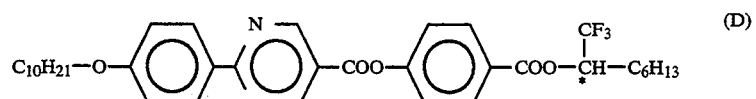

(1) Preparation of 1,1,1-trifluoro-2-octyl 4-benzyloxybenzoate

4-Benzyloxybenzoic acid chloride (1.23 g) was dissolved in methylene chloride (10 ml) and to the resulting solution was gradually added under ice cooling a solution of optically active 1,1,1-trifluoro-2-octanol (0.96 g), dimethylaminopyridine (0.55 g) and triethylamine (0.48 g) in methylene chloride (20 ml).

After the temperature of the reaction mixture was returned to room temperature, reaction was allowed to proceed for 24 hours and the resulting reaction mixture was poured into ice water and was extracted with methylene chloride. The methylene chloride layer was washed with dilute hydrochloric acid, water, 1N aqueous sodium carbonate solution and water in this order and dried over anhydrous magnesium sulfate and the solvent was distilled off to obtain a crude product. The product was subjected to toluene-silica gel column chromatography and was further recrystallized from ethanol to obtain the titled compound (18.4 g).

(2) Preparation of 1,1,1-trifluoro-2-octyl 4-hydroxybenzoate

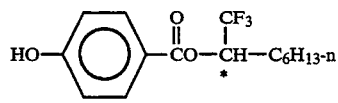

To the solution of the compound obtained in the above (1) in methanol (15 ml) was added 10% Pd carried on carbon (0.36 g) and tile mixture was subjected to hydrogenolysis reaction under hydrogen atmosphere to obtain the titled compound (1.43 g).

(3) Preparation of 4-(1,1,1-trifluoro-2-octyloxyycarbonyl)phenyl 2-(4-n-decyloxyphenyl)pyrimidine-5-ylcarboxylate

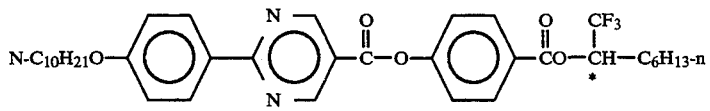

1,1,1-Trifluoro-2-octyl-4-hydroxybenzoate (0.50 g) prepared in the above (2) and triethylamine (0.15 g) were dissolved in methylene chloride (30 ml). Thereto was gradually added dropwise a solution of 2-(4-n-decyloxyphenyl) pyrimidine-5-yl -carboxylic acid chloride (0.63 g) in methylene chloride (30 ml).

Dimethylaminopyridine (0.05 g) in methylene chloride (5 ml) was added to the mixture obtained above, followed by stirring at room temperature for 24 hours. The reaction mixture was introduced into water and was made neutral and then, only the dichloromethane layer was extracted. This was dried over anhydrous magnesium sulfate and then, the solvent was distilled off. The residue was purified by column chromatography (developer: hexane/ethyl acetate=20/1 ) to obtain the titled product (0.59 g).

Optical rotation [α]$_{20}$$^D$=31.0°.

Phase transition temperatures (° C.) of the titled compound were observed under a polarizing microscope with a hot stage.

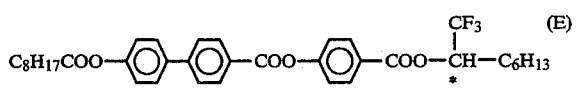

wherein S*(3) shows tristable state liquid crystal phase.

REFERENCE EXAMPLE 3

See Example 1 of EP 413 989 A2

Synthesis of the following compound

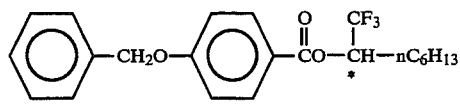

1) Synthesis of 1,1,1-trifluoro-2-octyl 4-benzyloxybenzoate

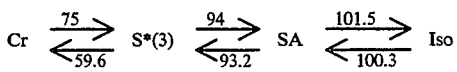

In 10 ml of methylene chloride was dissolved 1.23 g of 4-benzyloxybenzoic acid chloride, and a solution of 0.96 g of optically active 1,1,1-trifluoro-2-octanol, 0.55 g of dimethylaminopyridine, and 0.48 g of triethylamine in 20 ml or methylene chloride was added thereto in small portions under ice-cooling.

The reaction mixture was allowed to warm to room temperature and was reacted at that temperature for one day. The reaction mixture was poured into ice-water and extracted with methylene chloride. The methylene chloride phase was washed successively with diluted hydrochloric acid, water, 1N sodium carbonate aqueous solution, and water and dried over anhydrous magnesium sulfate. The solvent was removed by distillation to obtain a crude product. The crude product was purified by column chromatography using silica and toluene and then by recrystallization from ethanol to obtain 1.84 g of the titled compound.

2) Synthesis of 1,1,1-trifluoro-2-octyl 4-hydroxybenzoate

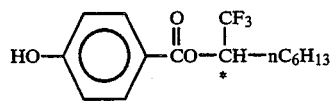

The compound obtained in 1) above was dissolved in 15 ml of ethanol, and 0.36 g of 10% palladium-on-carbon was added to the solution ko conduct hydrogenation in a hydrogen atmosphere to obtain 1.43 9 of the titled compound.

3) Synthesis of 4-(1,1,1-trifluoro-2-octyloxycarbonyl)phenyl 4'-n-nonanoyloxybiphenyl-4-carboxylate:

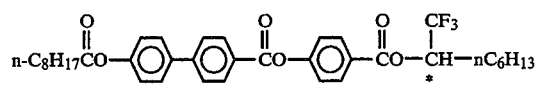

4'-n-Nonanoyloxybiphenyl-4-carboxylic acid (1.20 g) was refluxed together with an excess of thionyl chloride for 6 hours. The unaltered thionyl chloride was removed by distillation to obtain 4'-n-nonanoyloxydiphenylcarboxylic acid chloride.

The resulting acid chloride was dissolved in 12.0 ml of methylene chloride, and a solution of 1.00 g of the above-prepared 1,1,1-trifluorooctyl ester, 0.32 g of triethylamine, and 0.37 g of dimethylaminopyridine in 30 ml of methylene chloride was slowly added thereto under ice-cooling, and the mixture was allowed to react at room temperature for one day.

The reaction mixture was poured into ice-water and extracted with methylene chloride. The extract was washed successively with diluted hydrochloric acid, water, aqueous sodium carbonate solution, and water and dried over anhydrous sodium sulfate. The solvent was removed by distillation to obtain a crude product.

The crude product was purified by column chromatography using silica gel and toluene to obtain 1.1 g of the desired optically active compound.

Phase transition points (° C.) of the resulting compound were determined after recrystallization from absolute ethanol.

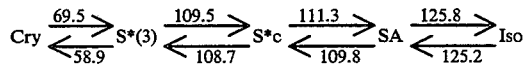

REFERENCE EXAMPLE 4

Synthesis of the following compound

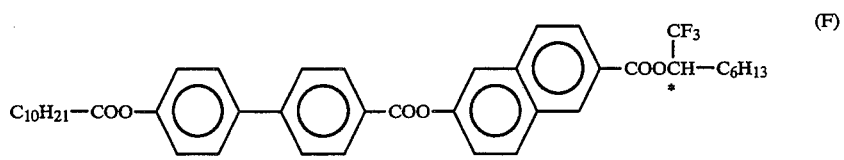

1) Synthesis of 1,1,1-trifluoro-2-octyl 6-benzyloxynaphthalene-2-carboxylate

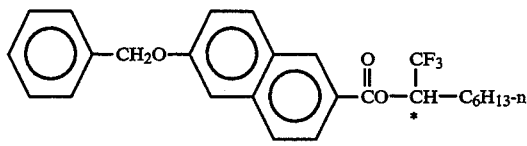

6-Benzyloxy-2-naphthoic acid chloride (5.3 g) was dissolved in methylene chloride (50 ml), and a solution of optically active 1,1,1-trifluoro-2-octanol (2.9 g), dimethylaminopyridine (0.6 9) and triethylamine (1.7 g) in methylene chloride (50 ml) was added to the naphthoic acid chloride solution in small portions under ice-cooling.

The reaction mixture was warmed to room temperature and allowed to react for 24 hours. The reaction solution was poured into ice-water and extracted with methylene chloride, and time methylene chloride phase was washed with dilute hydrochloric acid, water, 1N aqueous sodium carbonate solution and water in this sequence and dried over anhydrous magnesium sulfate. The solvent was removed by evaporation to give a crude product, which was purified by silica gel column chromatography (developer: toluene) and further recrystallized from ethanol to give the titled compound (3.8 g)

2) Synthesis of 1,1,1-trifluoro-2-octyl 6-hydroxynaphthalene-2-carboxylate

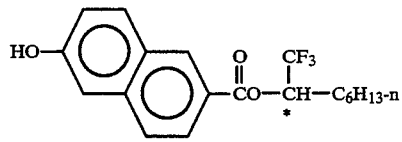

The compound obtained in 1) was dissolved in methanol (100 ml) and subjected to hydrogenolysis under a hydrogen atmosphere in the presence of 10% Pd on carbon (0.4 g) to give the titled compound (2.8 g).

3) Synthesis of 4'-n-undecanoyloxybiphenyl-4-carboxylic acid

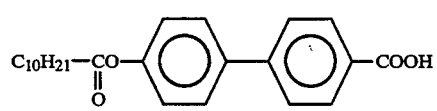

4'-Hydroxybiphenyl-4-carboxylic acid (3.5 g) and triethylamine (2.4 g) were dissolved in dichloromethane (30 ml). Undecanoyl chloride (4.3 g) and dimethylaminopyridine (0.2 g) were added to the solution, and the mixture was stirred at room temperature for about 20 hours. Dilute hydrochloric acid was added thereto, and the organic layer was separated in a separating funnel. The solvent was removed by evaporation, and the residue was dried after washing with n-hexane to give the titled compound (5 g).

4) Synthesis of 4'-n-undecanoyloxybiphenyl-4-carboxylic acid chloride

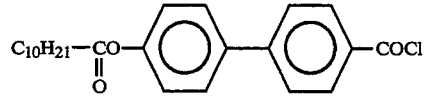

4-n-Undecanoyloxybiphenyl-4-carboxylic acid (5.0 g) was added to thionyl chloride (10 g), and N,N-dimethylformamide in a very small amount was added to the mixture. The resulting mixture was refluxed for 4 hours. The unaltered thionyl chloride was removed by evaporation to give the desired compound (5.2

5) Synthesis of 4'-undecanoyloxybiphenyl-4-carboxylic acid 6-(1,1,1-trifluoro-2-octyloxycarbonyl)naphthalene-2-ester

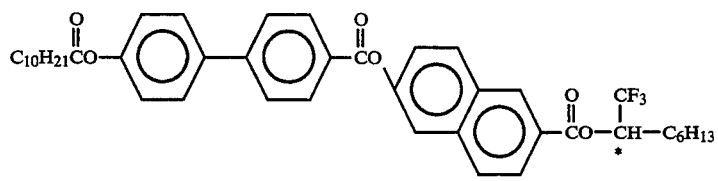

1,1,1-Trifluoro-2-octyl 6-hydroxynaphthalene-2-carboxylate (0.5 g) synthesized in 2) and triethylamine (0.16 g) were dissolved in 30 ml of methylene chloride. 4'-n-Undecanoyloxybiphenyl-4-carboxylic acid chloride (0.7 g) synthesized in 4) was dissolved in methylene chloride (30 ml) and the solution was added dropwise to the aforementioned solution. Dimethylaminopyridine (0.05 g) was further added, and the mixture was stirred at room temperature for 24 hours. The reaction mixture was poured into water, and the solution was neutralized before the methylene chloride layer was separated. After the organic layer was dried over anhydrous magnesium sulfate, methylene chloride was removed by evaporation, The residue was purified by silica gel column chromatography (development solvent: hexane/ethyl acetate=20/1) to give the desired compound (0.11 g), The phase transition temperatures (° C.) observed with a microscope equipped with a hot stage were as follows:

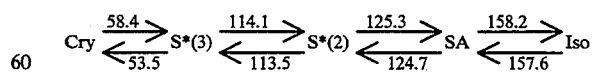

EXAMPLE 3

The substance comprising a mixture of equivalent amounts of compounds (A) and (C) showed the following phase transition temperatures (° C.) on the observation with a polarizing microscope equipped with a hot stage:

$$Sx \xrightleftharpoons[30]{60} S*I \xrightleftharpoons[65]{71} S*(3) \xrightleftharpoons[109.9]{110} S*c \xrightleftharpoons[128]{128} SA \xrightleftharpoons[158.9]{159.7} Iso$$

wherein
S*I: chiral smectic I phase, and
Sx: smectic phase in a high order.

Example 4

The substance comprising a mixture of equivalent amounts of compounds (B) and (C) showed the following phase transition temperatures (° C.) on the observation with a polarizing microscope equipped with a hot stage:

$$Cr \xrightleftharpoons[<17]{68} S*(3) \xrightleftharpoons[85]{86} S*c \xrightleftharpoons[114]{115} SA \xrightleftharpoons[140.4]{140} Iso$$

According to the present invention, a novel liquid crystal compound is provided, and the cost for preparing a tristable antiferroelectric liquid crystal composition can be reduced by adding the novel liquid crystal compound to the tristable antiferroelectric liquid crystal composition.

EXAMPLE 5

The substance comprising a mixture of equivalent amounts of compounds (A) and (D) showed the following phase transition temperatures (° C.) on the observation with a polarizing microscope equipped with a hot stage:

$$Cr \xrightleftharpoons[48]{} S*(3) \xrightleftharpoons[99.5]{} S*c \xrightleftharpoons[122.5]{} SA \xrightleftharpoons[142.0]{} Iso$$

EXAMPLE 6

The substance comprising a mixture of equivalent amounts of compounds (B) and (D) showed the following phase transition temperatures (° C.) on the observation with a polarizing microscope equipped with a hot stage:

$$Cr \xrightleftharpoons[46.2]{} S*(3) \xrightleftharpoons[78.0]{} S*c \xrightleftharpoons[103.0]{} SA \xrightleftharpoons[130.0]{} Iso$$

EXAMPLE 7

The substance comprising a mixture of equivalent amounts of compounds (A) and (E) showed the following phase transition temperatures (° C.) on the observation with a polarizing microscope equipped with a hot stage:

$$Cr \xrightleftharpoons[40]{} S*(3) \xrightleftharpoons[114.0]{} SA \xrightleftharpoons[154.1]{} Iso$$

EXAMPLE 8

The substance comprising a mixture of equivalent amounts of compounds (B) and (E) showed the following phase transition temperatures (° C.) on the observation with a polarizing microscope equipped with a hot stage:

$$Cr \xrightleftharpoons[45]{} S*(3) \xrightleftharpoons[102.8]{} SA \xrightleftharpoons[137.1]{} Iso$$

EXAMPLE 9

The substance comprising a mixture of equivalent amounts of compounds (A) and (F) showed the following phase transition temperatures (° C.) on the observation with a polarizing microscope equipped with a hot stage:

$$Cr \xrightleftharpoons[<25]{} S*(3) \xrightleftharpoons[114.5]{} S*c \xrightleftharpoons[134.0]{} SA \xrightleftharpoons[164.0]{} Iso$$

EXAMPLE 10

The substance comprising a mixture equivalent amounts of compounds (B) and (F) showed the following phase transition temperatures (° C.) on the observation with a polarizing microscope equipped with a hot stage:

$$Cr \xrightleftharpoons[<25]{} S*(3) \xrightleftharpoons[89.5]{} S*c \xrightleftharpoons[114.9]{} SA \xrightleftharpoons[155.5]{} Iso$$

We claim:

1. A diluent represented by the formula (I) for liquid crystal compounds which exhibit S*(3) phase and optically tristable states:

$$R^1-X-\phi-\phi-CO-O-\phi-CO-R^2 \quad (I)$$

wherein
$R^1$ represents and alkyl group having 3–20 carbon atoms,
$R^2$ represents a straight chain alkyl group having 3–20 carbon atoms and
X represents a group $$-\overset{O}{\underset{\|}{C}}O-, \ -\overset{O}{\underset{\|}{C}}-$$

or —O—.

2. A liquid crystal composition which exhibits the S*(3) phase with optically tristable states which comprises
  (a) about 50% by weight or more of antiferroelectric liquid crystal compounds; and
  (b) about 50% by weight or less of the liquid crystal compound represented by the general formula (I).

$$R^1-X-\phi-\phi-CO-O-\phi-CO-R^2 \quad (I)$$

wherein
$R_1$ means an alkyl group having 3–20 carbon atoms, $R_2$ means a straight chain alkyl group having 3–20 carbon atoms, and X means

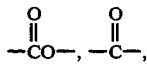

—O—, or a single bond.

3. A liquid crystal composition according to claim 2, wherein X represents —O— or a single bond.

4. A diluent represented by formula (I) for a liquid crystal compound which exhibits S*(3) phase and optically tristable states:

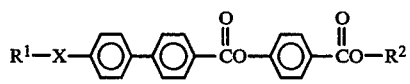

wherein $R^1$ represents a $C_3$ to $C_{20}$ alkyl group,
$R^2$ represents a straight chain $C_3$ to $C_{20}$ alkyl group, and
X is

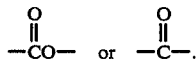

5. A liquid crystal composition according to claim 2, wherein X is

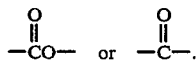

6. A process for preparing a liquid crystal composition which exhibits the S*(3) phase with optically tristable states which comprises:

diluting at least one antiferroelectric liquid crystal compound with an effective amount of at least one liquid crystal compound of the formula (I)

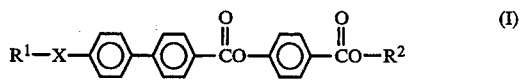

wherein $R^1$ means an alkyl having 3–20 carbon atoms, $R^2$ means a straight chain alkyl having 3–20 carbon atoms, and X means a group

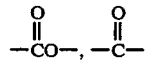

—O—, or a single bond.

7. A process according to claim 6, wherein said antiferroelectric liquid crystal compound is 4-(1,1,1-trifluoro-2-octyloxy-carbonyl)phenyl 4'-n-octyloxybiphenyl-4-carboxylate.

8. A process according to claim 6, wherein X is

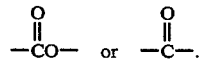

9. A liquid crystal composition which exhibits the S*(3) phase with optically tristable states which comprises
  (a) at least one antiferroelectric liquid crystal compound; and
  (b) at least one liquid crystal compound represented by the formula (I)

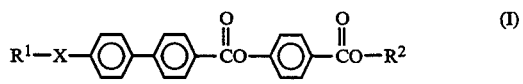

wherein $R^1$ means an alkyl group having 3–20 carbon atoms, $R^2$ means a straight chain $C_3$ to $C_{20}$ alkyl group, and X represents carbonyloxy, carbonyl, oxy, or a single bond.

* * * * *